United States Patent
Souda et al.

(10) Patent No.: US 6,441,220 B1
(45) Date of Patent: Aug. 27, 2002

(54) METHODS FOR PRODUCING CYCLOPROPANE CARBOXYLATES

(75) Inventors: Hiroshi Souda, Takatsuki; Kazunori Iwakura, Ibaraki, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/594,799

(22) Filed: Jun. 16, 2000

(30) Foreign Application Priority Data

Jun. 16, 1999 (JP) ........................ H11-169590

(51) Int. Cl.$^7$ .............................. C07C 69/74
(52) U.S. Cl. ........................ 560/124; 560/234
(58) Field of Search ................. 560/124, 234

(56) References Cited

U.S. PATENT DOCUMENTS

| | | | | |
|---|---|---|---|---|
| 3,647,857 A | * | 3/1972 | Morgan | 260/468 P |
| 3,873,716 A | * | 3/1975 | Fanta | 424/285 |
| 3,882,242 A | * | 5/1975 | Crawford | 424/305 |
| 3,976,663 A | * | 8/1976 | Fanta | 260/246.2 R |
| 4,053,629 A | * | 10/1977 | Fanta | 424/285 |
| 4,116,998 A | | 9/1978 | Makinson et al. | 260/465 |
| 4,283,414 A | * | 8/1981 | Harney et al. | 424/304 |
| T102,908 I4 | * | 4/1983 | Halpern et al. | 560/124 |
| 4,418,202 A | * | 11/1983 | Fayter, Jr. et al. | 549/496 |
| 4,976,892 A | * | 12/1990 | Jeromin et al. | 260/410.7 |

FOREIGN PATENT DOCUMENTS

| | | | | |
|---|---|---|---|---|
| DE | 2744641 | * | 4/1979 | C07C/69/54 |
| EP | 0992479 A1 | | 4/2000 | |
| FR | 2584611 | * | 1/1987 | C07C/69/54 |
| GB | 2005269 | * | 4/1979 | C07C/69/74 |
| JP | 52128336 | | 10/1977 | |
| JP | 52128337 | | 10/1977 | |
| JP | 53130627 | | 11/1978 | |
| JP | 53147040 | | 12/1978 | |
| JP | 5459265 | | 5/1979 | |
| JP | 5481235 | | 6/1979 | |
| JP | 7330671 | | 12/1995 | |
| JP | 9239270 | | 9/1997 | |

OTHER PUBLICATIONS

Chinese Journal of Chemistry, vol. 15, No. 1, 1997, pp. 90–93.
J. Org. Chem., vol. 61, 1996, pp. 3088–3090.
Bull. Chem. Soc. Jpn., vol. 66, No. 6, 1993, pp. 1863–1864.
Chem. Lett., vol. 3, No. 44, 1995, p. 246.
The 22nd Symposium on Rare Metal, 1993, p. 44.
M. Smith, "The Cyclopropane Group", Rodd's Chemistry of Carbon Compounds, Second Ed. (1967) Vol. II, Part A, Chapter 2, pp. 19–71.*
Aldrich Catalog Handbook of Fine Chemicals 1996–1997 (Aldrich Chemical Company).*
Michael P. Doyle et al, "Rearrangements of Oxocyclopropanecarboxylate Esters to Vinyl Ethers. Disparate Behavior of Transition–Metal Catalysts", J. Org. Chem., vol. 47 (1982), pp. 5326–5339.*

* cited by examiner

*Primary Examiner*—Paul J. Killos
(74) *Attorney, Agent, or Firm*—Birch, Stewart, Kolasch & Birch, LLP

(57) ABSTRACT

There is provided a method for producing a cyclopropanecarboxylate of formula (3):

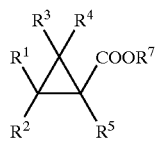

(3)

wherein $R^1$, $R^2$, $R^3$, $R^4$ and $R^5$ each independently represent:
  a hydrogen atom, halogen atom,
  an optionally substituted alkyl group and the like; and
$R^7$ represents:
  an optionally substituted alkyl group, and the like,
  which is characterized by
    reacting a cyclopropanecarboxylate of the formula (1)

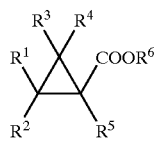

(1)

wherein $R^1$, $R^2$, $R^3$, $R^4$ and $R^5$ are as defined above, and
  $R^6$ represents an alkyl group having 1 to 10 carbon atoms or an optionally substituted phenyl group,
with a monohydroxy compound of the formula (2):

$$R^7OH \qquad (2)$$

wherein $R^7$ is the same as defined above,
in the presence of an alkali metal hydroxide.

9 Claims, No Drawings

METHODS FOR PRODUCING CYCLOPROPANE CARBOXYLATES

BACKGROUND OF THE INVENTION

1. Field of the Invention

The present invention relates to a method for producing a cyclopropanecarboxylate.

2. Description of Related Art

As for a method for producing a cyclopropanecarboxylic acid ester by transesterification reaction, for example, a method employing a sodium alkoxide catalyst has been disclosed (JP-A-52-128336) as well as a large number of the studies on the alkoxide catalysts of transition metals such as Ti (JP-A-52-128337, German Patent No. 2822472, British Patent No. 2005269).

However, in any of these transesterification reaction all catalysts required anhydrous conditions due to its stability in the presence of moisture, and hence should be stored, handled and reacted in an anhydrous condition, and thus they are not always satisfactory for an industrial manufacturing.

SUMMARY OF THE INVENTION

An object of the present invention is to provide a method for producing a cyclopropanecarboxylate readily in good yield by conducting a transesterification reaction between a cyclopropanecarboxylate and a monohydroxy compound in the presence of an alkali metal hydroxide, which method is advantageous in that said alkali metal hydroxide is not only inexpensive and readily available but also stable and can be readily handled.

Thus the present invention provides a method for producing a cyclopropanecarboxylate of formula (3):

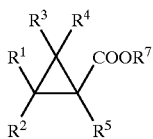

(3)

wherein $R^1$, $R^2$, $R^3$, $R^4$ and $R^5$ each independently represent:

a hydrogen atom, halogen atom, an optionally substituted alkyl group, an optionally substituted alkenyl group, an optionally substituted aralkyl group or an optionally substituted aryl group; and $R^7$ represents:

an optionally substituted alkyl group, an optionally substituted aralkyl group, or an optionally substituted aryl group, which comprises:

contacting a cyclopropanecarboxylate of the formula (1)

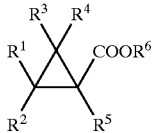

(1)

wherein $R^1$, $R^2$, $R^3$, $R^4$ and $R^5$ are as defined above, and
$R^6$ represents an alkyl group having 1 to 10 carbon atoms or an optionally substituted phenyl group,
with a monohydroxy compound of the formula (2):

$$R^7OH \qquad (2)$$

wherein $R^7$ is the same as defined above, in the presence of an alkali metal

DESCRIPTION OF THE PREFERRED EMBODIMENTS

The present invention is described in detail below.

The alkali metal hydroxide, employed as a catalyst, in the present invention include at least one selected from the hydroxides of Li, Na, K, Rb, Cs and Fr belonging to the alkali metal. Preferably, the hydroxides of Li, Na and K which are available readily at economical prices are employed, and lithium hydroxide is more preferred.

The alkali metal hydroxide is usually employed in an ahydrous form, but may be also used in a hydrated form such as $LiOH.H_2O$. In addition, the alkali metal hydroxide may be added as an aqueous solution and subsequently water contained therein may be removed, for example, by distillation prior to or during the reaction.

The amount of the alkali metal hydroxide to be used is not particularly limited and is usually 0.00001 to 2 moles, preferably 0.001 to 0.1 mole per mol of the cyclopropanecarboxylate of formula (1).

In the cyclopropanecarboxylate of formula (1), $R^1$, $R^2$, $R^3$, $R^4$ and $R^5$ each independently represent a hydrogen atom, a halogen atom, an optionally substituted alkyl group, an optionally substituted alkenyl group, an optionally substituted aralkyl or an optionally substituted aryl group.

The optionally substituted alkyl group includes, for example, an optionally substituted straight, branched or cyclic alkyl groups having 1 to 10 carbon atoms, which may be optionally substituted with a member selected from a halogen atom (e.g., fluorine, chlorine, bromine, idodine), a (C1–C3)alkoxy group (e.g. methoxy, ethoxy, n-propoxy, i-propoxy), a (C1–C5)alkoxycarbonyl group (e.g. methoxycarbony, ethoxycarbony, n-propoxycarbonyl, i-propoxycarbonyl, n-butoxycarbonyl, s-butoxycarbonyl, i-butoxycarbonyl, t-butoxycarbonyl, n-pentyloxycarbonyl and the like).

a (C1–C5)alkylsulfonyl group (e.g. methylsulfonyl, ethylsulfonyl, n-propylsulfonyl, n-butylsulfonyl, n-pentylsulfonyl and the like) and a hydroxyimino group of which hydrogen atom in the hydroxy group may be replaced by a member selected from a phenyl group, a (C1–C3)alkyl group, a (C3–C6)alkenyl group (e.g. allyl, methylallyl, butenyl, pentenyl, henexneyl and the like) and a (C3–C6) alkynyl group (e.g. propargyl, butynyl, pentynyl, hexynyl and the like).

Specific examples thereof include methyl, ethyl, n-propyl, i-propyl, n-butyl, sec-butyl, tert-butyl, n-pentyl, n-hexyl, cyclohexyl, menthyl, chloromethyl, dichloromethyl, trichloromethyl, bromomethyl, dibromomethyl, tribromomethyl, 1-chloroethyl, 2-chloroethyl, 1-bromoethyl, 2-bromoethyl, 1,2-dichloroethyl, 1,2-dibromoethyl, 2,2,2-trichloroethyl, 2,2,2-tribromoethyl, methoxymethyl, 2-methoxyethyl, phenoxyiminomethyl, methoxyiminomethyl, allyoxyiminomethyl, propargyloxyiminomethyl, hydroxyiminomethyl and the like.

The optionally substituted alkenyl group include a (C2–C5)alkenyl group optionally substituted with a member selected from a halogen atom, a phenyl group, a halo-substituted (C2–C4)alkenyl group (e.g. haloethylene, halotrimethylene, halotramethylene), a (C1–C5)alkoxycarbonyl group, a (C1–C5)alkylsulfonyl group, a (C1–C3)alkylsulfonyloxy group and a hydroxyimino group of which hydrogen atom in the hydroxy group may be replaced by a member selected from a phenyl group, a (C1–C3)alkyl group, a (C3–C6)alkenyl group and a (C3–C6)alkynyl group.

Specific examples thereof include vinyl, 1-methylvinyl, 1-propenyl, 2-methyl-1-propenyl, 2,2-dichlorovinyl, 2,2-dibromovinyl, 2-chloro-2-fluorovinyl, 2-chloro-2-trifluoromethylvinyl, 2-bromo-2-tribromomethylvinyl and the like.

The optionally substituted aralkyl group include a phenyl- or naphthyl-substituted (C1–C2)alkyl group which may be optionally substituted with a member selected from (C1–C10)alkyl group and a (C1–C6)alkoxy group (e.g., methoxy, ethoxy, n-propoxy, i-propoxy, n-butoxy, sec-butoxy, t-butoxy, cyclohexloxy and the like) or a halogen atom and the like on the phenyl or naphthyl ring.

Specific examples thereof include a benzyl, diphenylmethyl, phenylethyl, naphthylmethyl, naphthylethyl group and the like The optionally substituted aryl group include a phenyl or naphthyl group which may be optionally substituted with the above-described (C1–C10)alkyl group, a (C1–C10)alkoxy group or halogen atom and the like on the phenyl or naphthyl ring.

Specific examples thereof include phenyl, 1-naphthyl, 2-naphthyl and the like.

In the formula (1), $R^6$ represents an alkyl group having 1 to 10 carbon atoms or an optionally substituted phenyl group.

The alkyl group having 1 to 10 carbon atoms may be straight, branched or cyclic, and specific examples thereof include methyl, ethyl, n-propyl, i-propyl, n-butyl, sec-butyl, tert-butyl, n-pentyl, n-hexyl, cyclohexyl, n-heptyl, n-octyl, n-nonyl, menthyl and the like. Methyl and ethyl are preferred.

The phenyl group may be optionally substituted with a group selected from (C1–C10)alkyl group and (C1–C10) alkoxy group or a halogen atom and the like.

Specific examples of the cyclopropanecarboxylate of formula (1) include methyl cyclopropanecarboxylate,
methyl b 2-fluorocyclopropanecarboxylate,
methyl 2,2-dichlorocyclopropanecarboxylate,
methyl 2,2,3,3-tetramethylcyclopropanecarboxylate,
methyl 2,2-dimethyl-3-(1-propenyl) cyclopropanecarboxylate,
methyl 2,2-dimethyl-3-(2-methyl-1-propenyl) cyclopropanecarboxylate,
methyl 2,2-dimethyl-3-(3-methyl-2-butenyl) cyclopropanecarboxylate,
methyl 2,2-dimethyl-3-(2,2-dichlorovinyl) cyclopropanecarboxylate,
methyl 2,2-dimethyl-3-(2,2,2-trichloroethyl) cyclopropanecarboxylate,
methyl 2,2-dimethyl-3-(2-chloro-2-fluorovinyl) cyclopropanecarboxylate,
methyl 2,2-dimethyl-3-(2-bromovinyl) cyclopropanecarboxylate,
methyl 2,2-dimethyl-3-(2.2-dibromovinyl) cyclopropanecarboxylate,
methyl 2,2-dimethyl-3-(1,2,2,2-tetrabromoethyl) cyclopropanecarboxylate,
methyl 2,2-dimethyl-3-(1,2-dibromo-2,2-dichloroethyl) cyclopropanecarboxylate,
methyl 2,2-dimethyl-3-(2-chloro-3,3,3-trifluoro-1-propenyl)cyclopropanecarboxylate,
methyl 2,2-dimethyl-3-{3,3,3-trifluoro-2-(trifluromethyl-1-prophenyl}cyclopropanecarboxylate,
methyl 2,2-dimethyl-3-(2-phenyl-1-propenyl) cyclopropanecarboxylate,
methyl 2,2-dimethyl-3-(2-phenylvinyl) cyclopropanecarboxylate,
methyl 2,2-dimethyl-3-(2-methyl-3-phenyl-2-butenyl) cyclopropanecarboxylate,
methyl 2,2-dimethyl-3-{(2,2-difluorocycloproplyidene) methyl}cyclopropanecarboxylate,
methyl 2,2-dimethyl-3-{2-(t-butoxycarbonyl) vinyl}cyclopropanecarboxylate,
methyl 2,2-dimethyl-3-{2-fluoro-2-(methoxycarbonyl) vinyl}cyclopropanecarboxylate,
methyl 2,2-dimethyl-3-{2-fluoro-2-(ethoxycarbonyl) vinyl}cyclopropanecarboxylate,
methyl 2,2-dimethyl-3-{2-fluoro-2-(t-butoxycarbonyl) vinyl}cyclopropanecarboxylate,
methyl 2,2-dimethyl-3-[2-{2,2,2-trifluoro-1-(trifluoromethyl)ethoxycarbonyl}vinyl] cyclopropanecarboxylate,
methyl 2,2-dimethyl-3-(2-aza-2-methoxyvinyl) cyclopropanecarboxylate,
methyl 2,2-dimethyl-3-(2-aza-2-ethoxyvinyl) cyclopropanecarboxylate, methyl 2,2-dimethyl-3-(4-aza-4-methoxy-3-methylbuta-1,3-dienyl) cyclopropanecarboxylate,
methyl 2,2-dimethyl-3-[2-{(t-butyl)sulfonyl}-2-(t-butoxycarbonyl)vinyl]cyclopropanecarboxylate,
methyl 2,2-dimethyl-3-{2,2,2-tribromo-1-(methylsulfonyloxy)ethyl}cyclopropanecarboxylate,
methyl 2,2-dimethyl-3-{2,2-dibromo-2-(hydroxysulfinyl-1-(methoxy)ethyl}cyclopropanecarboxylate,
methyl 2,2-dimethyl-3-(methylsulfonyl)-3-{2-(t-butylsulfonyl-2-(t-butoxycarbonyl) ethyl}cyclopropanecarboxylate,
methyl 2,2-dimethyl-3-{2,2,2-tribromo-1-(methylsulfonyloxy)ethyl}cyclopropanecarboxylate,
methyl 2-methyl-2-ethyl-3-(1-propenyl) cyclopropanecarboxylate,
methyl 2,2-diethyl-3-(2,2-dichlorovinyl) cyclopropanecarboxylate,
methyl 2-methyl-2-phenyl-3-(2-methyl-1-propenyl) cyclopropanecarboxylate and those esters having an ethyl group, a butyl group, a menthyl group or the like in place of the methyl residue in any of the methyl cyclopropanecarboxylates above.

Preferred esters are 2,2-dimethyl-3-(2,2-dichlorovinyl) cyclopropanecarboxylate, 2,2-dimethyl-3-(2-aza-2-methoxyvinyl)cyclopropanecarboxylate, 2,2-dimethyl-3-(1-propenyl)cyclopropanecarboxylate and 2,2-dimethyl-3-(2-methyl-1-propenyl)cyclopropanecarboxylate.

$R^7$ in the monohydroxy compound of the formula (2) used in the present invention will be explained below.

The optionally substituted alkyl group include:
a (C1–C10)alkyl group which may be optionally substituted with a group selected from:
a halogen atom,
a (C3–C4)alkenyl group which may be substituted with a halogen atom,
a (C3–C4)alknyl group,
a (C5–C6)cycloalkyl group (e.g. cyclopentyl or cyclohexyl),
a (C5–C6)cycloalkenyl group (e.g. cyclopentenyl or cyclohexenyl group),
a heterocyclic group selected from:
a furyl group which may be substituted with a phenoxy group, a benzyl group, difluoromethyl group or a propynyl group,
a pyrrolyl group substituted with a propynyl group and optionally with a halomethyl group,
a thiazolyl group substituted with a halomethyl group or a halomethoxy group,
an isoxazolyl group optionally substituted with a methyl group,
a 4,5,6,7-tetrahydroisoindol-1,3-dione-2-yl group,
a 1-propynyl-imidazolidine-2,4-dione-3-yl group,
a pyrazolyl group substituted with a propyne group and a halomethyl group,
a halo-pyridyl group,
a thiazolin-2-one-5-yl group substituted with a methyl group and a propynyl group, and
a 1-prop-2-ynylindol-3-yl group substituted with a methyl or trifluoromethyl group;
a (C5–C6)oxocycloalkenyl group substituted with a methyl group and either a propenyl group or a propynyl group.

The optionally substituted aralkyl group include:
an optionally substituted (C6–C8)aralkyl group such as a phenyl-, naphthyl-, or anthracenyl-substituted (C1–C4) alkyl group, which phenyl-, naphthyl-, or anthracenyl group may be optionally substituted with a group selected from:
a nitro group, a cyano group, a halogen atom, a (C1–C10)alkyl group, a (C1–C3)haloalkyl group, a (C1–C3)alkoxy group, a (C1–C3)haloalkoxy group, a (C1–C3)alkoxy (C1–C3)alkyl group, an amino group, a (C3–C5)alkynyl group, a haloacetyloxy (C1–C3)alkyl group, a thienyl group, a phenyl group, and a phenoxy group which may be substituted with a halogen atom, and
said (C1–C4)alkyl group may be substituted with a cyano group or form a indanyl group with the phenyl group.

The optionally substituted aryl group include:
a phenyl or naphthyl group which may be optionally substituted with a group selected from a halogen atom, a (C1–C10)alkyl group, a (C1–C10)alkoxy group, a (C3–C5)alkynyl group, an acetyl group and an aldehyde group.

The monohydroxy compound of the formula (2) used in the present invention include alkyl alcohol, aralkyl alcohol, aryl alcohol, all of which may be optionally substituted.

Examples of the optionally substituted alkyl alcohol include:
a (C1–C10)alkyl alcohol compound such as methyl alcohol, ethyl alcohol, n-propyl alcohol, i-propyl alcohol, n-butyl alcohol, sec-butyl alcohol, tert-butyl alcohol, n-pentyl alcohol, neopentyl alcohol, amyl alcohol, n-hexyl alcohol, n-octyl alcohol and n-decyl alcohol;

a (C1–C10)alkyl substituted with a heterocyclic group as defined above such as
2-furylmethyl alcohol, 3-furylmethyl alcohol,
(5-phenoxy-3-furyl)methyl alcohol,
(5-benzyl-3-furyl)methane-1-ol,
[5-difluoromethyl)-3-furyl]methane-1-ol,
5-propargyl-2-furfuryl alcohol,
(5-methylisoxazol-3-yl)methane-1-ol,
1-[2-trifloromethyl)-1,3-thiazol-4-yl]prop-2-yn-1-ol,
1-[2-(trifluoromethoxy)-1,3-thiazol-4-yl]prop-2-yn-1-ol,
1-[1-prop-2-ynyl-5-(trifluoromethyl)pyrrol-3-yl]prop-2-yn-1-ol,
(1-prop-2-ynylpyrrrol-3-yl)methan-1-ol,
3-(hydroxymethyl)-1-propynyl-imidazolydine-2,4-dione,
2-(hydroxymethyl)-4,5,6,7-tetrahydroisoindole-1,3-dione,
[1-(2-propynyl)pyrrol-3-yl]methan-1-ol,
5-(hydroxymethyl)-4-methyl-(2-propynyl)-1,3-thiazolin-2-one,
[1-(2-propynyl)-5-(trifluoromethyl)-4-pyrazolyl]methan-1-ol,
(1-prop-2-ynyl-2-methylindol-3-yl)methane-1-ol,
[1-prop-2-ynyl-2-(trifluoromethyl)indol-3-yl]methane-1-ol, or
(2,3,6-trifluoro-4-pyridyl)methane-1-ol;
a (C1–C10)alkyl group which may be optionally substituted with a halogen atom such as
fluoroethyl alcohol, trifluoroethyl alcohol,
3,3-dibromo-2-propen-1-ol, hexafluoroisopropyl alcohol, perfluorobutyl alcohol,
perfluoropentyl alcohol, perfluorohexyl alcohol, perfluorooctyl alcohol,
perfluorodecyl alcohol;
a (C1–C10)alkyl group which may be substituted with a (C3–C4)alkenyl group, which alkenyl group may be substituted with a halogen atom, or a (C3–C4)alkynyl group such as
4-fluorohept-4-en-1-yn-3-ol, or
4-methylhept-4-en-1-yn-3-ol; and
a (C5–C6)oxocycloalkenyl group substituted with a methyl group and either a propenyl group or a propynyl group such as
4-hydroxy-3-methyl-2-(2-propenyl),2-cyclopentene-1-one, or 4-hydroxy-3-methyl-2-(2-propynyl)-2-cyclopentene-1-one.

In the optionally substituted alkyl groups of the alcohol compound of formula (2), preferred are substituted alkyl groups.

Examples of the optionally substituted aralkyl alcohol include:
benzyl alcohol,
2-methyl-3-phenylbenzyl alcohol,
2,3,5,6-tetrafluorobenzyl alcohol,
2,3,4,5,6-pentafluorobenzyl alcohol,
2,3,5,6-tetrafluoro-4-(methoxymethyl)benzyl alcohol,
2,3,5,6-tetrafluoro-4-methoxybenzyl alcohol,
6-chloro-2,3,4-trifluorobenzyl alcohol,
2-chloro-3,6-difluorobenzyl alcohol,
4-(trifluoromethyl)benzyl alcohol,
2,3,5,6-tetrafluoro-4-methylbenzyl alcohol,
3-phenylbenzyl alcohol, 2,6-dichlorobenzyl alcohol,
3-phenoxybenzyl alcohol,
2-hydroxy-2-(3-phenoxyphenyl)ethanenitrile,
2-hydroxy-2-[4-(methoxymethyl)phenyl]ethanenitrile,
2-[3-(4-chlorophenoxy)phenyl]-2-hydroxyethanenitrile,
2-(4-amino-2,3,5,6-tetrafluorophenyl)-2-hydroxyethanenitrile,
2-(4-fluoro-3-phenoxyphenyl)-2-hydroxyethanenitrile, (2-methylphenyl)methyl alcohol,
(3-methylphenyl)methyl alcohol,
(4-methylphenyl)methyl alcohol,
(2,3-dimethylphenyl)methyl alcohol,
(2,4-dimethylphenyl)methyl alcohol,
(2,5-dimethylphenyl)methyl alcohol,
(2,6-dimethylphenyl)methyl alcohol,
(3,4-dimethylphenyl)methyl alcohol,
(2,3,4-trimethylphenyl)methyl alcohol,
(2,3,5-trimethylphenyl)methyl alcohol,
(2,3,6-trimethylphenyl)methyl alcohol,
(3,4,5-trimethylphenyl)methyl alcohol,
(2,4,6-trimethylphenyl)methyl alcohol,
(2,3,4,5-tetramethylphenyl)methyl alcohol,
(2,3,4,6-tetramethylphenyl)methyl alcohol,
(2,3,5,6-tetramethylphenyl)methyl alcohol,
(pentamethylphenyl)methyl alcohol,
(ethylphenyl)methyl alcohol,
(n-propylphenyl)methyl alcohol,
(i-propylphenyl)methyl alcohol,
(n-butylphenyl)methyl alcohol,
(sec-butylphenyl)methyl alcohol,
(tert-butylphenyl)methyl alcohol,
(n-pentylphenyl)methyl alcohol,
(neopentylphenyl)methyl alcohol,
(n-hexylphenyl)methyl alcohol,
(n-octylphenyl)methyl alcohol,
(n-decylphenyl)methyl alcohol,
(n-dodecylphenyl)methyl alcohol,
(n-tetradecylphenyl)methyl alcohol, naphthylmethyl alcohol,
anthracenylmethyl alcohol, 1-phenylethyl alcohol,
1-(1-naphthyl)ethyl alcohol, 1-(2-naphtyl)ethyl alcohol,
(4-prop-2-ynylphenyl)methane-1-ol,
(3-prop-2-ynylphenyl)methane-1-ol,
4-prop-2-enylindane-1-ol, 4-phenylindane-2-ol,
4-(2-thienyl)indane-2-ol.

Examples of the optionally substituted aryl alcohol include phenol, 1-naphthol, 2-naphthol, 4-prop-2-ynylphenol, 3-prop-2-ynylphenol, 4-hydroxyacetophenone, 4-hydroxybenzaldehyde and the like, and compounds substituted with a (C1–C10)alkyl group, a (C1–C10)alkoxy group or halogen atom and the like on the aromatic ring.

Among the alcohol compound of the formula (2), a primary alcohol is preferred and more preferred is an alcohol wherein $R^7$ group is an optionally substituted phenylmethyl group, which phenyl group may be optionally substituted with a group selected from:

a nitro group, a cyano group, a halogen atom, a (C1–C10) alkyl group, a (C1–C3)haloalkyl group, a (C1–C3) alkoxy group, a (C1–C3)haloalkoxy group, a (C1–C3) alkoxy(C1–C3)alkyl group, an amino group, a (C3–C5) alkynyl group, a haloacetyloxy(C1–C3)alkyl group, a thienyl group, a phenyl group, and a phenoxy group which may be substituted with a halogen atom.

More specifically, 3-phenoxybenzyl alcohol is preferred.

An amount of the monohydroxy compound (2) is not particularly limited and may be, for example, one mole or more per mole of the cyclopropanecarboxylate (1), and also it may be used in excess amount or can be used as a solvent. The monohydroxy compound (2) in the reaction mixture can be recovered by, for example, an operation such as distillation and the like after completion of the reaction. Alternatively, the amount of the monohydroxy compound (2) may be not more than one mole per mole of the cyclopropanecarboxylate (1), and an appropriate operation as above may be conducted with a cyclopropanecarboxylate (1) in the reaction mixture after completion of the reaction.

The reaction of cyclopropanecarboxylate (1) with a monohydroxy compound (2) in the presence of an alkali metal hydroxide is usually carried out under an inert gas atmosphere such as argon, nitrogen and the like.

The reaction may be carried out at atmospheric pressure, increased pressure or reduced pressure, preferably at atmospheric pressure or reduced pressure.

The reaction is preferably conducted while removing an alcohol derived from cyclopropanecarboxylate (1) out of the reaction system continuously by a method such as distillation and the like when the resulting alcohol has a lower boiling point.

The reaction can be carried out without solvent or in an inert solvent, and examples of the solvent include halogenated hydrocarbons such as dichloromethane, chloroform, 1,2-dichloroethane and the like, aliphatic hydrocarbons such as hexane, heptane, octane, nonane and the like, aromatic hydrocarbons such as benzene, toluene, xylene, chlorobenzene and the like, ether solvents such as diethyl ether, tetrahydofuran, and the like.

An alcohol derived from cyclopropanecarboxylate (1) may be continuously removed by adding a solvent that forms an azeotrope with the alcohol.

The reaction temperature is not particularly restricted, and is usually in the range of 20 to 200° C.

According to the invention, by reacting an ester (1) and a monohydroxy compound (2) in the presence of an alkali metal hydroxide, the desired cyclopropanecarboxylate (3) can be readily and selectively obtained in a good yield, thus it is advantageous in an industrial manufacturing process.

EXAMPLES

The present invention is further explained by the following examples, which are not to be construed to limit the invention thereto.

Example 1

In a 20 ml three-necked flask were added 0.021 g of $LiOH.H_2O$, 2.26 g of methyl 2,2-dimethyl-3-(2,2-dichlorovinyl)cyclopropanecarboxylate and 6.17 g of 3-phenoxybenzyl alcohol, and the mixture was stirred for 12 hours at 110° C. Analysis of the reaction mixture by a gas chromatography revealed that the yield of (3-phenoxyphenyl)methyl 2,2-dimethyl-3-(2,2-dichlorovinyl)cyclopropanecarboxylate was 98% based on the starting ester.

Example 2

In a 50 ml three-necked flask were added 0.084 g of $LiOH.H_2O$, 4.48 g of methyl 2,2-dimethyl-3-(2,2-dichlorovinyl)cyclopropanecarboxylate, 8.03 g of 3-phenoxybenzyl alcohol and 9.00 g of n-heptane. The mixture was stirred for 6 hours at a heptane refluxing temperature, while a by-product methanol being azeotropically removed with heptane. Analysis of the reaction mixture by a gas chromatography revealed that the yield of (3-phenoxyphenyl)methyl 2,2-dimethyl-3-(2,2-dichlorovinyl)cyclopropanecarboxylate was 98% based on the starting ester.

Example 3

In a 50 ml three-necked flask were added 0.084 g of $LiOH.H_2O$, 8.93 g of methyl 2,2-dimethyl-3-(2,2-dichlorovinyl)cyclopropanecarboxylate, 10.03 g of 3-phenoxybenzyl alcohol and 18.0 g of n-heptane. The mixture was stirred for 6 hours at a heptane refluxing temperature, while a by-product methanol being azeotropically removed with heptane. Analysis of the reaction mixture by a gas chromatography revealed that the yield of (3-phenoxyphenyl)methyl 2,2-dimethyl-3-(2,2-dichlorovinyl)cyclopropanecarboxylate was 98% based on the starting ester.

Example 4

Except for using 0.48 g of a 10% aqueous solution of LiOH instead of 0.084 g of LiOH.H₂O, the reaction was conducted in a similar manner as in Example 3. The reaction mixture was analyzed by a gas chromatography, which revealed that the yield of (3-phenoxyphenyl)methyl 2,2-dimethyl-3-(2,2-dichlorovinyl)cyclopropanecarboxylate was 98% based on the starting ester.

Example 5

In a 100 ml three-necked flask were added 0.096 g of LiOH, 17.85 g of methyl 2,2-dimethyl-3-(2,2-dichlorovinyl)cyclopropanecarboxylate, 16.04 g of 3-phenoxybenzyl alcohol and 17.9 g of n-heptane. The mixture was stirred for 22 hours at a heptane refluxing temperature, while a by-product methanol being azeotropically removed with heptane. Analysis of the reaction mixture by a gas chromatography revealed that the yield of (3-phenoxyphenyl)methyl 2,2-dimethyl-3-(2,2-dichlorovinyl)cyclopropanecarboxylate was 97% based on the starting ester.

Example 6

In a 100 ml three-necked flask were added 0.096 g of LiOH, 17.89g of methyl 2,2-dimethyl-3-(2,2-dichlorovinyl)cyclopropanecarboxylate, 16.09 g of 3-phenoxybenzyl alcohol and 17.9 g of xylene. The mixture was stirred for 12 hours at a xylene refluxing temperature. Analysis of the reaction mixture by a gas chromatography revealed that the yield of (3-phenoxyphenyl)methyl 2,2-dimethyl-3-(2,2-dichlorovinyl)cyclopropanecarboxylate was 95% based on the starting ester.

Example 7

Except for using 0.020 g of NaOH instead of 0.021 g of LiOH-H₂O, the reaction was conducted in a similar manner as in Example 1. Analysis of the reaction mixture by a gas chromatography revealed that the yield of (3-phenoxyphenyl)methyl 2,2-dimethyl-3-(2,2-dichlorovinyl)cyclopropanecarboxylate was 93% based on the starting ester.

Example 8

In a 30 ml two-necked flask were added 0.007 g of LiOH.H₂O, 0.30 g of methyl 2,2-dimethyl-3-(1-propenyl)cyclopropanecarboxylate, 0.36 g of 3-phenoxybenzyl alcohol and 2.0 g of toluene, and the mixture was stirred for 8 hours at a toluene refluxing temperature. Analysis of the reaction mixture by a gas chromatography showed that the yield of (3-phenoxyphenyl)methyl 2,2-dimethyl-3-(1-propenyl)cyclopropanecarboxylate was 99% based on the starting ester.

Example 9

In a 30 ml two-necked flask were added 0.007 g of LiOH.H₂O, 0.33 g of methyl 2,2-dimethyl-3-(2-aza-2-methoxyvinyl)cyclopropanecarboxylate, 0.36 g of 3-phenoxybenzyl alcohol and 2.0 g of toluene, and the mixture was stirred for 8 hours at a toluene refluxing temperature. Analysis of the reaction mixture by a gas chromatography showed that the yield of (3-phenoxyphenyl)methyl 2,2-dimethyl-3-(2-aza-2-methoxyvinyl)cyclopropanecarboxylate was 83% based on the starting ester.

Example 10

In a 30 ml two-necked flask were added 0.004 g of LiOH.H₂O, 0.31 g of methyl 2,2-dimethyl-3-(2-methyl-1-propenyl)cyclopropanecarboxylate, 1.00 g of (2,3,4,5,6-pentafluorophenyl)methyl alcohol and 0.6 g of toluene, and the mixture was stirred for 8 hours at a toluene refluxing temperature. Analysis of the reaction mixture by a gas chromatography showed that the yield of (2,3,4,5,6-pentafluorophenyl)methyl 2,2-dimethyl-3-(2-methyl-1-propenyl)cyclopropanecarboxylate was 92% based on the starting ester.

Example 11

In a 30 ml two-necked flask were added 0.004 g of LeOH.H₂O, 0.40 g of methyl 2,2-dimethyl-3-(2,2-dichlorovinyl)cyclopropanecarboxylate, 1.00 g of (2,3,4,5,6-pentafluorophenyl)methyl alcohol and 0.8 g of toluene, and the mixture was stirred for 8 hours at a toluene refluxing temperature. Analysis of the reaction mixture by a gas chromatography showed that the yield of (2,3,4,5,6-pentafluorophenyl)methyl 2,2-dimethyl-3-(2,2-dichlorovinyl)-cyclopropanecarboxylate was 84% based on the starting ester.

Example 12

In a 30 ml two-necked flask were added 0.004 g of LiOH.H₂O, 0.40 g of methyl 2,2-dimethyl-3-(2-aza-2-methoxyvinyl)cyclopropanecarboxylate, 1.00 g of (2,3,4,5,6-pentafluorophenyl)methyl alcohol and 0.8 g of toluene, and the mixture was stirred for 8 hours at a toluene refluxing temperature 21. Analysis of the reaction mixture by a gas chromatography showed that the yield of (2,3,4,5,6-pentafluorophenyl)methyl 2,2-dimethyl-3-(2-aza-2-methoxyvinyl)cyclopropanecarboxylate was 88% based on the starting ester.

Example 13

The reaction was conducted in a similar manner as in Example 12 except that 0.004 g of NaOH was used in place of LiOH.H₂O. Analysis of the reaction mixture by a gas chromatography showed that the yield of (2,3,4,5,6-pentafluorophenyl)methyl 2,2-dimethyl-3-(2-aza-2-methoxyvinyl)cyclopropanecarboxylate was 78% based on the starting ester.

What is claimed is:

1. A method for producing cyclopropanecarboxylate of the formula (3):

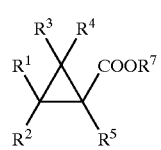

(3)

wherein $R^1$, $R^2$, $R^3$, $R^4$ and $R^5$ each independently represent:
  a hydrogen atom, a halogen atom,
  an optionally substituted alkyl group,
  an optionally substituted alkenyl group,
  an optionally substituted aralkyl group or
  an optionally substituted aryl group; and
$R^7$ represents:
  an optionally substituted alkyl group,
  an optionally substituted aralkyl group, or
  an optionally substituted aryl group,
  which comprises:

reacting a cyclopropanecarboxylate of the formula (1)

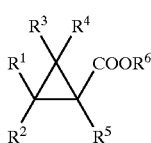

(1)

wherein $R^1$, $R^2$, $R^3$, $R^4$ and $R^5$ are as defined above, and $R^6$ represents an alkyl group having 1 to 10 carbon atoms or an optionally substituted phenyl group,
with a monohydroxy compound of the formula (2):

$$R^7OH \quad (2)$$

wherein $R^7$ is the same as defined above, in the presence of an alkali metal hydroxide that is LiOH or LiOH.H$_2$O.

2. The method according to claim 1, wherein $R^1$, $R^2$, $R^3$, $R^4$ and $R^5$ each independently represent:
  a hydrogen atom, a halogen atom,
  an optionally substituted straight, branched or cyclic alkyl group having 1 to 10 carbon atoms, which alkyl group may be optionally substituted with a member selected from:
    a halogen atom, a (C1–C3) alkoxy group,
    a (C1–C5)alkoxycarbonyl group, a (C1–C5) alkylsulfonyl group and a hydroxyimino group of which hydrogen atom in the hydroxy group may be replaced by a member selected from a phenyl group, a (C1–C3)alkyl group, a (C3–C6)alkenyl group and a (C3–C6)alkynyl. group,
  a (C2–C5)alkenyl group optionally substituted with a member selected from a halogen atom, a phenyl group, a halo-substituted (C2–C4)alkylene group, a (C1–C5)alkoxycarbonyl group, a (C1–C5) alkylsulfonyl group, a (C1–C3)alkylsulfonyloxy group and a hydroxyimino group of which hydrogen atom in the hydroxy group may be replaced by a member selected from a phenyl group, a (C1–C3) alkyl group, a (C3–C6)alkenyl group and a (C3–C6) alkynyl group,
  a phenyl- or naphthyl-substituted (C1–C2)alkyl group, the phenyl or naphthyl substituent of which may be optionally substituted with a member selected from a (C1–C10)alkyl group, a halogen atom and a (C1–C6) alkoxy group, or
  a phenyl or naphthyl group which may be optionally substituted with a (C1–C10)alkyl group, a (C1–C10) alkoxy group of a halogen atom;
$R^6$ represents:
  an alkyl group having 1 to 10 carbon atoms or
  a phenyl group which may be optionally substituted with a group selected from (C1–C10)alkyl group and (C1–C10)alkoxy group or a halogen atom;
$R^7$ represents:
  a (C1–C10)alkyl group which may be optionally substituted with a group selected from:
    a halogen atom,
    a (C3–C4)alkenyl group which may be substituted with a halogen atom,
    a (C3–C4)alkynyl group,
    a (C5–C6)cycloalkyl group,
    a (C5–C6)cycloalkenyl group,
    a heterocyclic group selected from:
      a furyl group which may be substituted with a phenoxy group, a benzyl group, difluoromethyl group or a propynyl group,
      a pyrrolyl group substituted with a propynyl group and optionally with a halomethyl group,
      a thiazolyl group substituted with a halomethyl group or a halomethoxy group,
      an isoxazolyl group optionally substituted with a methyl group,
      a 4,5,6,7-tetrahydroisoindol-1,3-dione-2-yl group,
      a 1-propynyl-imidazolidine-2,4-dione-3-yl group,
      a pyrazolyl group substituted with a propynyl group and a halomethyl group,
      a halo-pyridyl group,
      a thiazolin-2-one-5-yl group substituted with a methyl group and a propynyl group, and
      a 1-prop-2-ynylindol-3-yl group substituted with a methyl or trifluoromethyl group;
  a (C5–C6)oxocycloalkenyl group substituted with a methyl group and either a propynyl group or a propenyl group;
  a phenyl-, naphthyl-, or anthracenyl-substituted (C1–C4) alkyl group which may be optionally substituted with a group selected from:
    a nitro group, a cyano group, a halogen atom, a (C1–C10)alkyl group, a (C1–C3)haloalkyl group, a (C1–C3)alkoxy group, a (C1–C3)haloalkoxy group, a (C1–C3)alkoxy(C1–C3)alkyl group, an amino group, a (C3–C5)alkynyl group, a haloacetyloxy (C1–C3)alkyl group, a thienyl group, a phenyl group, and a phenoxy group which may be substituted with a halogen atom, and
  said (C1–C4)alkyl group may be substituted with a cyano group or form an indanyl group with the phenyl group; or
  a phenyl or naphthyl group which may be optionally substituted with a group selected from a halogen atom, a (C1–C10)alkyl group, a (C1–C10)alkoxy group, a (C3–C5)alkynyl group, an acetyl group and an aldehyde group.

3. The method according to claim 1, wherein $R^6$ in cyclopropanecarboxylate of the formula (1) represents a methyl or ethyl group.

4. The method according to claim 3, wherein the cyclopropanecarboxylate of the formula (1) represent 2,2-dimethyl-3-(2,2-dichlorovinyl)cyclopropanecarboxylate.

5. The method according to claim 3, wherein the cyclopropanecarboxylate of the formula (1) is 2,2-dimethyl-3-(2-methyl-1-propenyl)cyclopropanecarboxylate.

6. The method according to claim 3, wherein the cyclopropanecarboxylate of the formula (1) is 2,2-dimethyl-3-(1-propenyl)cyclopropanecarboxylate.

7. The method according to claim 1, wherein the cyclopropanecarboxylate of the formula (1) is 2,2-dimethyl-3-(2-aza-2-methoxyvinyl)cyclopropanecarboxylate.

8. The method according to claim 2, wherein $R^7$ represents an optionally substituted phenylmethyl group, which phenyl group may be optionally substituted with a group selected from:
  a nitro group a cyano group, a halogen atom, a (C1–C10) alkyl group, a (C1–C3)haloalkyl group, a (C1–C3) alkoxy group, a (C1–C3)haloalkoxy group, a (C1–C3) alkoxy (C1–C3)alkyl group, an amino group, a (C3–C5)alkynyl group, a haloacetyloxy (C1–C3)alkyl group, a thienyl group, a phenyl group, and a phenoxy group which may be substituted with a halogen atom.

9. The method according to claim 7, wherein the monohydroxy compound of the formula (2) is 3-phenoxybenzyl alcohol.

* * * * *